United States Patent [19]

Papay et al.

[11] 4,237,020
[45] Dec. 2, 1980

[54] LUBRICATING AND FUEL COMPOSITIONS CONTAINING SUCCINIMIDE FRICTION REDUCERS

[75] Inventors: Andrew G. Papay, Manchester; Joseph P. O'Brien, Kirkwood, both of Mo.

[73] Assignee: Edwin Cooper, Inc., St. Louis, Mo.

[21] Appl. No.: 67,999

[22] Filed: Aug. 20, 1979

[51] Int. Cl.$^3$ .............................................. C10M 1/38
[52] U.S. Cl. ...................................... 252/47.5; 44/63
[58] Field of Search ............................ 252/47.5; 44/63

[56] References Cited

U.S. PATENT DOCUMENTS

| | | | |
|---|---|---|---|
| 3,172,892 | 3/1965 | Le Suer | 260/326.5 |
| 3,219,666 | 11/1965 | Norman et al. | 252/51.5 A X |
| 3,381,022 | 4/1968 | Le Suer | 260/404.8 |
| 3,390,086 | 6/1968 | O'Halloran | 252/47.5 |
| 3,459,518 | 8/1969 | Mehmedbasich | 44/63 |
| 3,522,179 | 7/1970 | Le Suer | 252/51.5 A |
| 3,634,241 | 1/1972 | Lowe | 44/63 X |
| 3,715,368 | 2/1973 | Mehmedbasich | 44/63 X |
| 3,852,205 | 12/1974 | Kablaoui et al. | 252/47.5 |

Primary Examiner—Andrew Metz
Attorney, Agent, or Firm—Donald L. Johnson; Robert A. Linn; Joseph D. Odenweller

[57] ABSTRACT

Engine fuel economy is improved by including in the crankcase oil a friction-reducing amount of an N-aliphatic hydrocarbyl hydroxyalkylsulfinylsuccinimide or N-aliphatic hydrocarbyl hydroxyalkylsulfonylsuccinimide. The additives can also be added to the engine fuel.

10 Claims, No Drawings

LUBRICATING AND FUEL COMPOSITIONS CONTAINING SUCCINIMIDE FRICTION REDUCERS

BACKGROUND OF THE INVENTION

In order to conserve energy, automobiles are now being engineered to give improved gasoline mileage compared to those in recent years. This effort is of great urgency as a result of Federal regulations recently enacted which compel auto manufacturers to achieve prescribed gasoline mileage. These regulations are to conserve crude oil. In an effort to achieve the required mileage, new cars are being down-sized and made much lighter. However, there are limits in this approach beyond which the cars will not accommodate a typical family.

Another way to improve fuel mileage is to reduce engine friction. The present invention is concerned with this latter approach.

SUMMARY

According to the present invention, engine friction is lowered by adding to the engine crankcase oil or fuel a small friction-reducing amount of a N-$C_{10-36}$ aliphatic hydrocarbyl hydroxyalkylsulfinylsuccinimide or N-$C_{10-36}$ aliphatic hydrocarbyl hydroxyalkylsulfonylsuccinimide.

DESCRIPTION OF THE PREFERRED EMBODIMENTS

A preferred embodiment of the invention is a lubricating oil composition containing a friction-reducing amount of oil-soluble additive having the formula

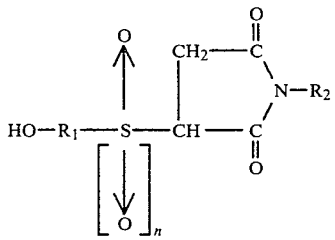

wherein $R_1$ is a divalent aliphatic hydrocarbon group containing 1 to about 6 carbon atoms, $R_2$ is an aliphatic hydrocarbon group containing about 10-36 carbon atoms, and n is 0 or 1.

Representative examples of these additives are:
N-decyl-[(2-hydroxyethyl)sulfinyl]succinimide
N-(2-ethylhexyl)-[(4-hydroxybutyl)sulfinyl]succinimide
N-dodecyl-[(2-hydroxyethyl)sulfinyl]succinimide
N-octadecyl-[(2-hydroxypropyl)sulfinyl]succinimide
N-(2-ethyltetradecyl)-[(2-hydroxybutyl)sulfinyl]succinimide
N-eicosyl-[(2-hydroxyethyl)sulfinyl]succinimide
N-tetracosyl-[(2-hydroxypropyl)sulfinyl]succinimide
N-triacontyl-[(2-hydroxyethyl)sulfinyl]succinimide
N-(2-hexyltriacontyl)-[(2-hydroxyethyl)sulfinyl]succinimide
N-(hexatriacontyl)-[(4-hydroxybutyl)sulfinyl]succinimide
N-decenyl-[(2-hydroxyethyl)sulfinyl]succinimide
N-(1-octyldecenyl)-[(2-hydroxyethyl)sulfinyl]succinimide
N-octadecenyl-[(2-hydroxyethyl)sulfinyl]succinimide
N-docosenyl-[(2-hydroxybutyl)sulfinyl]succinimide
N-(1-decyldocosenyl)-[(2-hydroxyethyl)sulfinyl]succinimide
N-hexatriacontenyl-[(2-hydroxypropyl)sulfinyl]succinimide
N-decyl-[(2hydroxyethyl)sulfonyl]succinimide
N-(2-ethylhexyl)-[(4-hydroxybutyl)sulfonyl]succinimide
N-dodecyl-[(2-hydroxyethyl)sulfonyl]succinimide
N-octadecyl-[(2-hydroxypropyl)sulfonyl]succinimide
N-(2-ethyltetradecyl)-[(2-hydroxybutyl)sulfonyl]succinimide
N-eicosyl-[(2-hydroxyethyl)sulfonyl]succinimide
N-tetracosyl-[(2-hydroxypropyl)sulfonyl]succinimide
N-triacontyl-[(2-hydroxyethyl)sulfonyl]succinimide
N-(2-hexyltriacontyl)-[(2-hydroxyethyl)sulfonyl]succinimide
N-(hexatriacontyl)-[(4-hydroxybutyl)sulfonyl]succinimide
N-decenyl-[(2-hydroxyethyl)sulfonyl]succinimide
N-(1-octyldecenyl)-[(2-hydroxyethyl)sulfonyl]succinimide
N-octadecenyl-[(2-hydroxyethyl)sulfonyl]succinimide
N-docosenyl-[(2-hydroxybutyl)sulfonyl]succinimide
N-(1-decyldocosenyl)-[(2-hydroxyethyl)sulfonyl]succinimide
N-hexatriacontenyl-[(2-hydroxypropyl)sulfonyl]succinimide In a more preferred embodiment $R_1$ is —$CH_2CH_2$— forming a 2-hydroxyethyl group. In a highly preferred embodiment $R_1$ forms a hydroxyethyl group and $R_2$ is an aliphatic hydrocarbyl group containing about 12-20 carbon atoms. Highly preferred additives are:
N-oleyl-[(2-hydroxyethyl)sulfinyl]succinimide and
N-oleyl-[(2-hydroxyethyl)sulfonyl]succinimide.

The additives are readily made by reacting an appropriate $C_{10-36}$ aliphatic hydrocarbyl primary amine with maleic anhydride on about equal mole basis at about 10°–30° C. Then about one mole of a tert-amine (e.g. triethylamine) is added forming a triethylammonium N-($C_{10-36}$ hydrocarbyl) maleamate. This is then reacted with the appropriate mercapto alkanol to form triethylammonium 3-(hydroxyalkylthio)succinamate. This is then heated to about 160° C. under vacuum to remove water, any solvents used and the trialkylamine forming N-($C_{10-36}$ hydrocarbyl)-3-(hydroxyalkylthio)succinimide. This is then oxidized using hydrogen peroxide to form either N-($C_{10-36}$ hydrocarbyl)-(hydroxyalkylsulfinyl)succinimide or N-($C_{10-36}$ hydrocarbyl)-(hydroxyalkylsulfonyl)succinimide depending upon whether one or two moles of hydrogen peroxide are used per mole of thio intermediate. The oxidation can be carried out in methanol solvent at about 30°–50° C.

The following example illustrates the method of making the additives.

EXAMPLE 1

In a reaction vessel was placed 196 grams of maleic anhydride and 900 ml acetone. The mixture was stirred under nitrogen to dissolve the maleic anhydride. Then 534 grams of oleylamine was added dropwise over one hour at 17°–21° C. Then 220 grams triethylamine was added dropwise over 30 minutes at 21°–22° C. Then 156 grams 2-mercaptoethanol were added over a 30 minute period at 22°–26° C. The reaction mixture was heated to 100° C. to distill off acetone and then to 160° C. under 30″ Hg vacuum to remove triethylamine and water yielding 853 grams of N-oleyl-[(2-hydroxyethyl)thio]-succinimide.

In a reaction vessel was placed 413 grams of the above intermediate and 400 grams of methanol. The mixture was stirred at 40° C. under nitrogen to form a solution and then 91 grams of 30% hydrogen peroxide was added over a 30-45 minute period at about 55° C. Solvent was distilled off up to 100° C. and then 30″ Hg vacuum applied to complete removal of volatiles leaving 422 grams of N-oleyl-3-[2-hydroxyethyl)sulfinyl]-succinimide.

The corresponding sulfonyl additive can be made following the above procedure using twice the amount of hydrogen peroxide. Likewise, other mercapto alkanols may be used to form the hydroxyalkylsulfinyl or sulfonyl substituents. Alternatively, different hydrocarbyl amines can be substituted forming the corresponding N-hydrocarbyl group.

The additives are added to lubricating oil in an amount which reduces the friction of an engine operating with the oil in the crankcase. A useful concentration is about 0.05-3 wt %. A more preferred range is about 0.1-1.5 wt %.

From the above it can be seen that the present invention provides an improved crankcase lubricating oil. Accordingly, an embodiment of the invention is an improved motor oil composition formulated for use as a crankcase lubricant in an internal combustion engine wherein the improvement comprises including in the crankcase oil an amount sufficient to reduce fuel consumption of the engine of an oil-soluble additive as described herein.

The additives can be used in mineral oil or in synthetic oils of viscosity suitable for use in the crankcase of an internal combustion engine. Crankcase lubricating oils have a viscosity up to about 80 SUS at 210° F. According to the present invention the additives function to increase fuel economy when added to lubricating oil compositions formulated for use in the crankcase of internal combustion engines. Similar mileage benefits could be obtained in both spark ignited and diesel engines.

Crankcase lubricating oils of the present invention have a viscosity up to about SAE 40. Sometimes such motor oils are given a classification at both 0° and 210° F., such as SAE 10W 40 or SAE 5W 30.

Mineral oils include those of suitable viscosity refined from crude oil from all sources including Gulfcoast, midcontinent, Pennsylvania, California, Alaska and the like. Various standard refinery operations can be used in processing the mineral oil.

Synthetic oil includes both hydrocarbon synthetic oil and synthetic esters. Useful synthetic hydrocarbon oils include liquid polymers of $\alpha$-olefins having the proper viscosity. Especially useful are the hydrogenated liquid oligomers of $C_{6-12}$ $\alpha$-olefins such as $\alpha$-decene trimer. Likewise, alkylbenzenes of proper viscosity can be used, such as didodecylbenzene.

Useful synthetic esters include the esters of both monocarboxylic acid and polycarboxylic acid as well as monohydroxy alkanols and polyols. Typical examples are didodecyl adipate, trimethylol propane tripelargonate, pentaerythritol tetracaproate, di-(2-ethylhexyl)adipate, dilauryl sebacate and the like. Complex esters prepared from mixtures of mono- and dicarboxylic acid and mono- and polyhydroxyl alkanols can also be used.

Blends of mineral oil with synthetic oil are particularly useful. For example, blends of 5-25 wt % hydrogenated $\alpha$-decene trimer with 75-95 wt % 150 SUS (100° F.) mineral oil results in an excellent lubricant. Likewise, blends of about 5-25 wt % di-(2-ethylhexyl)adipate with mineral oil of proper viscosity results in a superior lubricating oil. Also blends of synthetic hydrocarbon oil with synthetic esters can be used. Blends of mineral oil with synthetic oil are especially useful when preparing low viscosity oil (e.g. SAE 5W 20) since they permit these low viscosities without contributing excessive volatility.

The more preferred lubricating oil composition includes zinc dihydrocarbyldithiophosphate (ZDDP) in combination with the present additives. Both zinc dialkyldithiophosphates and zinc dialkaryldithiophosphates as well as mixed alkyl-aryl ZDDP are useful. A typical alkyl-type ZDDP contains a mixture of isobutyl and isoamyl groups. Zinc dinonylphenyldithiophosphate is a typical aryl-type ZDDP. Good results are achieved using sufficient ZDDP to provide about 0.01-0.5 wt % zinc. A preferred concentration supplies about 0.05-0.3 wt % zinc.

Another additive used in the oil compositions are the alkaline earth metal petroleum sulfonates or alkaline earth metal alkaryl sulfonates. Examples of these are calcium petroleum sulfonates, magnesium petroleum sulfonates, barium alkaryl sulfonates, calcium alkaryl sulfonates or magnesium alkaryl sulfonates. Both the neutral and the overbased sulfonates having base numbers up to about 400 can be beneficially used. These are used in an amount to provide about 0.05-1.5 wt % alkaline earth metal and more preferably about 0.01-1.0 wt %. In a most preferred embodiment the lubricating oil composition contains a calcium petroleum sulfonate or alkaryl (e.g. alkylbenzene) sulfonate.

Viscosity index improvers can be included such as the polyalkylmethacrylate type or the ethylene-propylene copolymer type. Likewise, styrene-diene VI improvers or styrene-acrylate copolymers can be used. Alkaline earth metal salts of phosphosulfurized polyisobutylene are useful.

Most preferred crankcase oils also contain an ashless dispersant such as the polyolefin-substituted succinamides and succinimides of polyethylene polyamines such as tetraethylenepentamine. The polyolefin succinic substituent is preferably a polyisobutene group having a molecular weight of from about 800 to 5,000. Such ashless dispersants are more fully described in U.S. Pat. Nos. 3,172,892 and 3,219,666 incorporated herein by reference.

Another useful class of ashless dispersants are the polyolefin succinic esters of mono- and polyhydroxyl alcohols containing 1 to about 40 carbon atoms. Such dispersants are described in U.S. Pat. Nos. 3,381,022 and 3,522,179.

Likewise, mixed ester/amides of polyolefin substituted succinic acid made using alkanols, amines and/or aminoalkanols represent a useful class of ashless dispersants.

The succinic amide, imide and/or ester type ashless dispersants may be boronated by reaction with a boron compound such as boric acid. Likewise the succinic amide, imide, and/or ester may be oxyalkylated by reaction with an alkylene oxide such as ethylene oxide or propylene oxide.

Other useful ashless dispersants include the Mannich condensation products of polyolefin-substituted phenols, formaldehyde and polyethylene polyamine. Preferably, the polyolefin phenol is a polyisobutylene-substituted phenol in which the polyisobutylene group has a molecular weight of from about 800 to 5,000. The preferreed polyethylene polyamine is tetraethylene pentamine. Such Mannich ashless dispersants are more fully described in U.S. Pat. Nos. 3,368,972; 3,413,347; 3,442,808; 3,448,047; 3,539,633; 3,581,598; 3,600,372; 3,634,515; 3,697,574; 3,703,536; 3,704,308; 3,725,480; 3,726,882; 3,736,357; 3,751,365; 3,756,953; 3,793,202; 3,798,165; 3,798,247 and 3,803,039.

The above Mannich dispersants can be reacted with boric acid to form boronated dispersants having improved corrosion properties.

Superior results are obtained by using the present additives in lubricating oil in combination with a phosphonate additive. Preferred phosphonates are the di-$C_{1-4}$ alkyl $C_{12-36}$ alkyl or alkenyl phosphonates. These compounds have the structure:

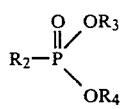

wherein $R_2$ is an aliphatic hydrocarbon group containing about 12–36 carbon atoms and $R_3$ and $R_4$ are independently selected from lower alkyl groups containing about 1–4 carbon atoms. Representative examples of these synergistic coadditives are:
dimethyl octadecylphosphonate
dimethyl octadecenylphosphonate
diethyl 2-ethyldecylphosphonate
ethyl propyl 1-butylhexadecylphosphonate
methyl ethyl octadecylphosphonate
methyl butyl eicosylphosphonate
dimethyl hexatriacontylphosphonate
When using the phosphonate coadditive only a small synergistic amount is required. A useful range is about 0.005–0.75 wt % based on the formulated oil. A more preferred amount is about 0.05–0.5 wt %.

The friction-reducing additives of this invention are also useful in liquid hydrocarbon fuel compositions. Fuel injected or inducted into a combustion chamber wets the walls of the cylinder. Fuels containing a small amount of the present additive reduce the friction due to the piston rings sliding against the cylinder wall.

The additives can be used in both diesel fuel and gasoline used to operate internal combustion engines. Fuels containing about 0.001–0.25 wt % of the present additives can be used.

Fuels used with the invention can contain any of the additives conventionally added to such fuels. In the case of gasoline it can include dyes, antioxidants, detergents, antiknocks (e.g. tetraethyllead, methylcyclopentadienyl manganese tricarbonyl, rare earth metal chelates, methyl tert-butylether and the like). In the case of diesel fuels the compositions can include pour point depressants, detergents, ignition improvers (e.g. hexylnitrate) and the like.

Tests were conducted which demonstrated the friction-reducing properties of the present invention.

SAE-2 Friction Machine Test

In this test a heavy fly wheel is rotated at 1440 rpm. A series of 9 clutch plates are then brought to bear axially at a defined load against the fly wheel. The fly wheel is connected to the rotating plates. The stationary plates are connected to a device which measures rotational torque. The time from initially applying pressure through the clutch plate until the rotating plate ceases to rotate is measured. Also, the rotational torque measured at the stationary plates is plotted against time. Torque rises initially to a value referred to as "dynamic torque" and then rises finally to a value called "static torque." The clutch plates are immersed in test lubricant. A reduction in friction is indicated by (1) an increase in time required to bring rotation to a halt and (2) a decrease in dynamic and static torque. Results are reported in percent time increase (percent improvement) and percent reduction in dynamic and static torque compared to that obtained using the same oil without the test additive.

The test oil is a fully formulated oil of SAE SE quality. Test results are given in the following table. In the table the test additive was used at 0.3 wt % and the phosphonate coadditive at 0.2 wt %.

| Additive | SAE 2 | | |
|---|---|---|---|
| | Time | Dynamic | Static |
| N-oleyl-(2-hydroxyethyl)sulfinylsuccinimide | 11% | 10% | 20% |
| N-oleyl-(2-hydroxyethyl)sulfinylsuccinimide + dimethyl octadecylphosphonate | 14% | 15% | 31% |

The results show a significant reduction in friction which is further improved by use of the phosphonate coadditive.

We claim:
1. A lubricating oil composition comprising an oil lubricating viscosity and containing a friction-reducing amount of an oil-soluble additive having the formula

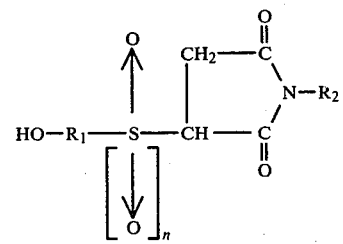

wherein $R_1$ is a divalent aliphatic hydrocarbon group containing 1 to about 6 carbon atoms, $R_2$ is an aliphatic hydrocarbon group containing about 10–36 carbon atoms, and n is 0 or 1.

2. A composition of claim 1 wherein n is 0.
3. A composition of claim 2 wherein $R_1$ is —$CH_2C-H_2$—.
4. A composition of claim 3 wherein $R_2$ contains about 12–20 carbon atoms.
5. A composition of claim 4 wherein $R_2$ is oleyl.
6. A composition of claim 1 wherein n is 1.
7. A composition of claim 6 wherein $R_1$ is —$CH_2C-H_2$—.
8. A composition of claim 7 wherein $R_2$ contains about 12–20 carbon atoms.
9. A composition of claim 8 wherein $R_2$ is oleyl.
10. A liquid hydrocarbon fuel suitable for use in an internal combustion engine containing a friction-reducing amount of a fuel-soluble additive having the formula

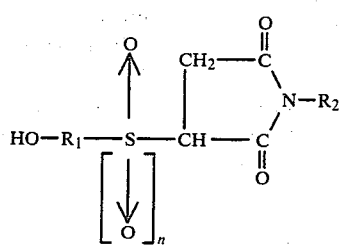
wherein $R_1$ is a divalent aliphatic hydrocarbon group containing 1 to about 6 carbon atoms, $R_2$ is an aliphatic hydrocarbon group containing about 10-36 carbon atoms, and n is 0 or 1.
* * * * *